United States Patent [19]
Löbberding et al.

[11] Patent Number: 5,616,731
[45] Date of Patent: Apr. 1, 1997

[54] PHOTOCHEMICAL LABELLING OF NUCLEIC ACIDS WITH DIGOXIGENIN REAGENTS AND THEIR USE IN GENE PROBE TEST SYSTEMS

[75] Inventors: Antonius Löbberding, Wuppertal; Gamal K. Mikhail, Odenthal; Wolfgang Springer, Wuppertal, all of Germany

[73] Assignee: Bayer Aktiengesellschaft, Leverkusen, Germany

[21] Appl. No.: 468,452

[22] Filed: Jun. 6, 1995

Related U.S. Application Data

[63] Continuation of Ser. No. 86,600, Jul. 1, 1993, abandoned.

[30] Foreign Application Priority Data

Jul. 7, 1992 [DE] Germany .................... 42 22 254.0

[51] Int. Cl.$^6$ ................... C07D 493/04; C07D 493/06
[52] U.S. Cl. ............................................. 549/282
[58] Field of Search ................................ 549/282

[56] References Cited

U.S. PATENT DOCUMENTS

| | | | |
|---|---|---|---|
| 4,950,744 | 8/1990 | Dattagupta et al. | 536/27 |
| 5,099,031 | 3/1992 | Mikhail et al. | 548/454 |
| 5,198,537 | 3/1993 | Huber et al. | 530/406 |

FOREIGN PATENT DOCUMENTS

| | | |
|---|---|---|
| 0187332 | 7/1986 | European Pat. Off. . |
| 0324474A1 | 7/1989 | European Pat. Off. . |
| 0324474B1 | 7/1989 | European Pat. Off. . |
| 0324468 | 7/1989 | European Pat. Off. . |

OTHER PUBLICATIONS

J. Albarella et al., Nucl. Acids Res., 17: 4293–4308 (1989).
K. Kaufman et al., J. Org. Chem., 45: 738–740 (1980).
W. Wulff et al., J. Am. Chem. Soc., 110: 7419–7434 (1988).
J.A. Matthews, L.J. Kricka, Analytical Biochemistry 169, 1–25 (1988).
U. Landegren, R. Kaiser, C.T. Caskey, L. Hood, Science 242, 229 (1988).
N. Dattagupta, P.M.M. Rae. E.D. Huguenel, E. Carlson, A. Lyga, J.S. Shapiro, J.P. Albarella, Analytical Biochemistry 177, 85 (1989)
J.P. Albarell, R.L. Minegar, W.L. Patterson, N. Dattagupta, E. Carlson, Nucleic Acids Research 17, 4293 (1989).
J.J. Leary, D.J. Brigati, D.C. Ward, Proc. Natl. Acad. Sci. USA 80, 4045–4049 (1983).
G.G. Schmitz, T. Walter, R. Seibl, C. Kessler, Analytical Biochemistry 192, 222–231 (1991).
C. Kessler, H.-J. Höltke, R. Seibl, J. Burg, K. Mühlegger, Biol. Chem. Hoppe–Seyler 371, 917–927 (1990).
Annals of the New York Academy of Sciences, vol. 346, 1980, pp. 355–367.
Biological Chemistry Hoppe–Seyler, vol. 371, No. 10, Oct. 1990, pp. 917–927.
Analytical Biochemistry, vol. 192, No. 1, Jan. 1991, pp. 222–231.
Dyes and Pigments, vol. 14, Nr. 4, 1990, "Synthesis and Application of Reactive Dyes with Heterocyclic Reactive Systems", 239–263.

*Primary Examiner*—Ba K. Trinh
*Attorney, Agent, or Firm*—Sprung Horn Kramer & Woods

[57] ABSTRACT

The present invention concerns photochemical labelling reagents comprising a digoxigenin derivative and a furocoumarin derivative bound via a spacer. The labelling reagent can be used in gene diagnostic.

3 Claims, No Drawings

PHOTOCHEMICAL LABELLING OF NUCLEIC ACIDS WITH DIGOXIGENIN REAGENTS AND THEIR USE IN GENE PROBE TEST SYSTEMS

This application is a continuation of application Ser. No. 08/086,600, filed Jul. 1, 1993, now abandoned.

Gene probe diagnostics is a method for the sequence-specific detection of DNA/RNA sequences. It is based on the hybridisation of the gene probe sequence with complementary sequence regions of the DNA/RNA to be detected (J. A. Matthews, L. J. Kricka, Analytical Biochemistry 169, 1–25 (1988); U. Landegren, R. Kaiser, C. T. Caskey, L. Hood, Science 242, 229 (1988)).

Gene probe diagnostics makes possible the detection of infectious diseases and genetic defects. Prerequisites for the broad application of gene probe diagnostics are adequate sensitivity of detection, simplicity in performance and the avoidance of radioactivity.

One variant of gene probe diagnostics proceeds by way of the direct photochemical labelling of the DNA/RNA to be detected; subsequently hybridisation occurs to gene probes with complementary nucleic acid sequences (N. Dattagupta, P. M. M. Rae, E. D. Huguenel, E. Carlson, A. Lyga, J. S. Shapiro, J. P. Albarella, Analytical Biochemistry 177, 85 (1989); J. P. Albarella, R. L. Minegar, W. L. Patterson, N. Dattagupta, E. Carlson, Nucleic Acids Research 17, 4293 (1989)).

Furocoumarins which are linked to biotin by way of suitable spacer molecules have been shown to be very suitable for the photobiotinylation of nucleic acids. After hybridisation to a gene probe with a complementary nucleic acid sequence, and a separation step, detection takes place, for example by addition of a complex of antibiotin antibody or avidin or streptavidin with alkaline phosphatase. For the detection, a colour reaction, which is elicited by alkaline phosphatase, is carried out in an additional step (J. J. Leary, D. J. Brigati, D. C. Ward, Proc. Natl. Acad. Sci. USA 80, 4045–4049 (1983)).

One disadvantage of the detection system using biotin is the wide distribution of biotin in biological systems. This disadvantage is avoided by using, for example, digoxigenin instead of biotin. In this case, the detection reaction takes place using digoxigenin antibody.

Current methods for labelling nucleic acids with digoxigenin proceed enzymatically or photochemically (G. G. Schmitz, T. Walter, R. Seibl, C. Kessler, Analytical Biochemistry 192, 222–231 (1991); C. Kessler, H.-J. Höltke, R. Seibl, J. Burg, K. Mühlegger, Biol. Chem. Hoppe-Seyler 371, 917–927 (1990)). In the case of photolabelling with the photodigoxigenin reagent from Boehringer (EP-324 474-A), irreversible denaturation has been observed of the nucleic acids to be detected.

Surprisingly, no denaturation of the nucleic acids has been observed in photoreactions with digoxigenin reagents which are linked to furocoumarins by means of a suitable spacer.

In the present invention, the synthesis is described of digoxigenin derivatives which are linked to furocoumarins by means of suitable spacers, and their use for labelling nucleic acids is investigated.

According to the invention, a labelling reagent of the general formula:

Dig—S—Fu is synthesised, where

Dig=digoxigenin derivative as a hapten,

S=a spacer molecule, and

Fu=a furocoumarin derivative as a photochemically linkable structure.

The digoxigenin derivative (Dig) is a chemically modified derivative of the steroid in which the C-3 hydroxyl group is modified with a chemically linkable substituent. This can be a carboxyl, thio, amino or hydroxyl grouping, or an activated form thereof. Digoxigenin and derivatives thereof are commercially available, for example, from Boehringer Mannheim GmbH of Mannheim, Germany. Methods for preparation of digoxigenin derivatives are described in U.S. Pat. No. 5,198,537, which issued Mar. 30, 1993, to Huber et al.

Suitable furocoumarins and spacers are described in EP 187 332.

The spacer is a polyalkylamine, polyethylene glycol or a combination thereof.

Polyalkylamines have the following general formula:

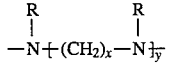

where:

R represents H, $C_1$–$C_7$-alkyl, aryl (such as, for example, phenyl, naphthyl or anthracyl), hydroxyl or $C_1$–$C_7$-alkoxy;

x represents a number between 2 and 7;

y represents a number between 3 and 10.

R can occur differently in the possible variants mentioned above, i.e. R need not be identical for each repetition of the —$(CH_2)_x$—N—R unit in the spacer. The same is also the case for x, i.e. x must not be the same number for each repetition of the —$(CH_2)_x$— unit in the spacer.

Preferably the Rs, independently of each other, =H, $C_1$–$C_4$-alkyl (e.g. methyl, ethyl, n-propyl, i-propyl, n-butyl, i-butyl, tert-butyl); x=2, 3, 4 or 5; and y=3, 4, 5 or 6.

Particvularly preferred are $N^4,N^9$-dimethylspermine derivatives of the formula:

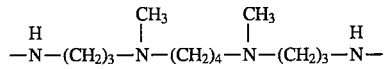

Polyethylene glycols have the following general formula:

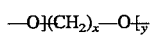

where x is=a number between 2 and 7 and y is=a number between 3 and 10.

Preferred are polyethylene glycols with x=2, 3, 4 or 5; y=3, 4, 5 or 6. Particularly preferred are polyethylene glycols with x=2 and y=4, 5 or 6.

Spacer molecules with combined amine/glycol structures have the following general formula:

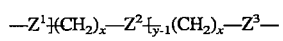

where $Z^1$, $Z^2$ and $Z^3$ independently of each other, represent O or NR,

R represents H, $C_1$–$C_7$-alkyl, aryl (such as, for example, phenyl, naphthyl or anthryl), hydroxyl or $C_1$–$C_7$-alkoxy;

x represents a number between 2 and 7;

y represents a number between 3 and 10.

Preferred are spacer structures with $Z^2$=O and $Z^1$, $Z^3$=NR, where R=H, $C_1$–$C_4$-alkyl (e.g. methyl, ethyl, n-propyl, i-propyl, n-butyl, i-butyl, tert-butyl); x=2, 3, 4 or 5; and y=3, 4, 5 or 6.

Particularly preferred are structures with $Z^2=O$, $Z^1$, $Z^3=NR$, where R=H, methyl, ethyl; x=2; and y=4.

Methods suitable for preparing spacers are known from the literature. For example, the preparation of N-4, N-9-dimethylspermine is described by Albarella et al, *Nuc. Acid. Res.*, 17: 4293 (1989). The preparation involves reaction of a diaminoalkane with with acrylonitrile followed by hydrogenation. A similar procedure is described by U.S. Pat. No. 4,950,744, which issued Aug. 21, 1990, to Dattagupta et al. See examples 3 and 4 therein. Other polyalkylamine spacers can be prepared analogously.

As also taught in U.S. Pat. No. 4,950,744, polyethylene glycol spacers are known, for example, from Kern et al, *Makromol. Chem.*, 150: 2539 (1979). Other polyethylene glycol spacers can be prepared in a manner analogous to the known methods.

Diaminopolyalkylene glycol spacers can be prepared by reaction of polyethylene glycols with ammonia.

Suitable photochemically linkable structures are, in particular, furocoumarins, such as, for example, angelicin (isopsoralen) or psoralens and derivatives thereof which react photochemically with nucleic acids.

Angelicin derivatives have the following general formula:

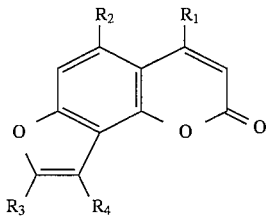

where $R_1$, $R_2$ and $R_3$, independently of each other, represent H or $C_1$–$C_7$-alkyl, and $R_4$ represents H, $C_1$–$C_7$-alkyl or a low alkyl with hydroxyl, $C_1$–$C_7$-alkoxy, amino, halo or N-phthalimido substituents.

Particularly preferred are angelicin derivatives which contain the following $R_1$–$R_4$ groupings;

| $R_1$ | $R_2$ | $R_3$ | $R_4$ |
|---|---|---|---|
| H | H | H | H |
| $CH_3$ | H | $CH_3$ | H |
| $CH_3$ | $CH_3$ | $CH_3$ | $CH_2OH$ |
| $CH_3$ | H | $CH_3$ | $CH_2OCH_3$ |
| $CH_3$ | H | $CH_3$ | $CH_2NH_2$ |
| H | H | $CH_3$ | $CH_2Cl$ |
| H | H | $CH_3$ | |

Other compounds with different Rs may also be synthesised by processes known from the literature.

Suitable psoralens have the following general formula:

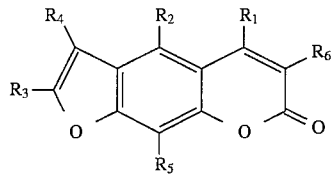

where $R_1$, $R_3$ and $R_6$, independently of each other, represent H or $C_1$–$C_7$-alkyl, $R_4$ represents H, $C_1$–$C_7$-alkyl or $C_1$–$C_7$-alkyl with hydroxyl, $C_1$–$C_7$-alkoxy, amino, halo or N-phthalimido substituents, $R_2$ and $R_5$, independently of each other, represent H, hydroxyl, carboxyl, carbo-$C_1$–$C_7$-alkoxy or $C_1$–$C_7$-alkoxy.

Angelicin derivatives are advantageous in comparison with psoralens because of the monoadduct formation.

EP 187 332 mentions a number of literature references that describe the synthesis of furocoumarins and teaches elsewhere that other furocoumarins can be synthesized following published procedures. Therefore, the foregoing furocoumarins are either already known or they can be prepared in manner analogous to the known furocoumarins. For example, according to EP 187 332, angelicin is described by Venema et al, *Mol. Gen. Genet.*, 179: 1 (1980); 4,5'-dimethylangelicin by Vedaldi et al, *Chem. Biol. Interact.*, 36: 275 (1981); psoralen by Marciani et al, *Naturforsch B*, 27: 196 (1972); 8-methoxypsoralen by Belognzov et al, *Mutat. Res.*, 84: 11 (1981), and by Scott et al, *Photochem. Photobiol.*, 34: 63 (1981); 5-aminomethyl-8-methoxypsoralen by Hansen et al, *Tet. Lett.*, 22: 1847 (1981); 4,5,8-trimethylpsoralen by Ben-Hur et al, *Biochem. Biophys. Acta*, 331: 181 (1973); and 4'-aminomethyl-4,5,8-trimethylpsoralen by Issacs et al, *Biochem.*, 16: 1058 (1977).

Other references, which are not mentioned in EP 187 332, but disclose synthesis schemes suitable for preparing furocoumarins, include Kaufman et al, *J. Org. Chem.*, 45: 738 (1980); Wulff et al, *J. Am. Chem. Soc.*, 110: 7419 (1988); U.S. Pat. No. 4,950,744, which issued Aug. 21, 1990, to Dattagupta et al; and U.S. Pat. No. 5,099,031, issued Mar. 24, 1992, to Mikhail et al.

The sequence of the linkage of the digoxigenin, the spacer and the furocoumarin is arbitrary. It is thus possible, inter alia, first to link the digoxigenin Dig to the spacer S and subsequently to react the product with the furocoumarin Fu. Conversely, Fu-S may first be constructed and then reacted with Dig.

The linking of the moieties is effected in a manner known per se.

EXAMPLE 1

Preparation of amino(hexaethylene glycol)angelicin (amino-PEG-angelicin 3)

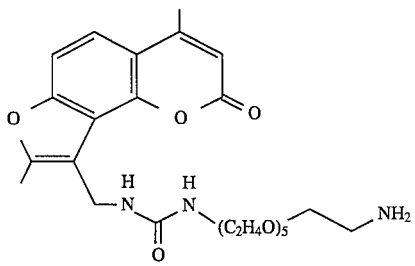

4.87 g (20 mmol) of 4-aminomethyl-4,5'-dimethylangelicin are dissolved in 25 ml of DMF and reacted with 3.24 g (20 mmol) of carbonyldiimidazole at room temperature.

Complete reaction (according to TLC) was observed after 6 hours of stirring under nitrogen. The solution is slowly added dropwise to a solution of 16.85 g (60 mmol) of 1,17-diamino-3,6,9,12,15-pentaoxaheptadecane in 40 ml of DMF at 80° C. and the mixture stirred at 70° C. for a further 12 hours. After cooling, the solution is concentrated in vacuo and chromatographed on silica gel (eluent: chloroform/methanol/ammonia 90:10:1, $R_f$=0.28). 7.1 g (65% of theory) are obtained of a slightly yellow oil.

EXAMPLE 2

Preparation of $N^1$-(angelicinamido)-$N^4,N^9$-dimethylspermine (2)

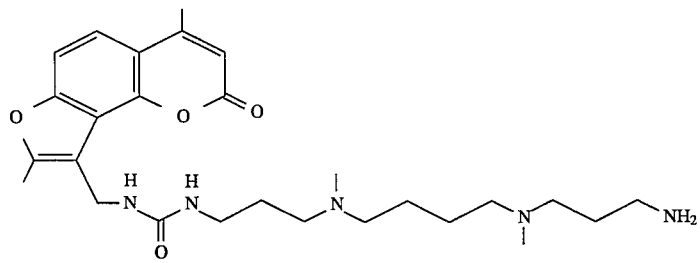

4.87 g (20 mmol) of 4-aminomethyl-4,5'-dimethylangelicin are activated with carbonyldiimidazole in an analogous manner to Example 1. The resulting solution is added dropwise to a solution of 13.8 g (60 mmol) of $N^4,N^9$-dimethylspermine in 40 ml of DEF in analogy with Example 1. After cooling, the solution is concentrated in vacuo and the residue is chromatographed on silica gel (eluent: chloroform/methanol/ammonia 30:5:11, $R_f$=0.11). 7.1 g (71% of theory) are obtained of a yellow oil.

EXAMPLE 3

Preparation of digoxigenin-PEG-angelicin (Dig-PA, 3)

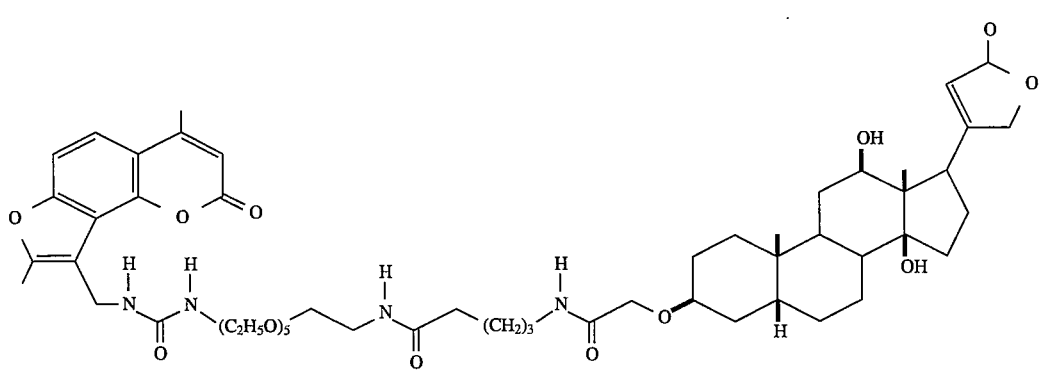

13.7 mg (0.03 mmol) of amino-PEG-angelicin 1 are dissolved in 2 ml of chloroform (for spectroscopy). A solution of 18.9 mg (0.03 mmol) of N-hydroxysuccinimide digoxigenin-3-O-methylcarbonyl-ε-aminocaproate (Dig-NHS) in 2 ml of chloroform is added dropwise. After stirring for 24 hours at room temperature, the reaction is complete (according to TLC). The solution is concentrated in vacuo and the residue is chromatographed on silica gel (eluent: chloroform/methanol/ammonia 90:10:1, $R_f$=0.45). 21 mg (77% of theory) are obtained of a slightly yellow solid with a melting point of 63° to 65° C.

EXAMPLE 4

Preparation of digoxigenin-spermine-angelicin (Dig-SpA, 4)

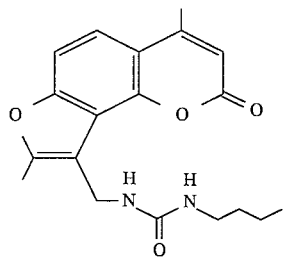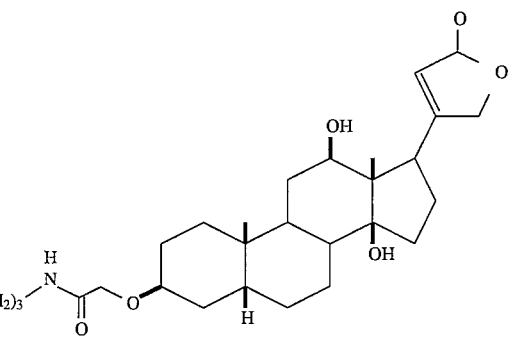

15 mg (0.03 mmol) of the compound 2 described in Example 2 are reacted with 19.8 mg (0.03 mmol) of N-hydroxysuccinimide digoxigenin-3-O-methylcarbonyl-ε-aminocaproate (Dig-NHS) in analogy with Example 3.

After working up and column chromatography on silica gel (eluent: chloroform/methanol/anunonia 30:5:1, $R_f$=0.25), 24 mg (77% of theory) are obtained of a weakly yellowish solid with a melting point of 106° to 109° C.

EXAMPLE 5

Photoreaction of hairpin oligonucleotides with DigPA

50 μg of the hairpin oligonucleotide are taken up in 100 μl of Tris-HCl buffer. The solution is left in a water bath at 50° C. for 15 minutes. In order to be cooled slowly to room temperature, the sample is taken out of the water bath. Subsequently, a further 400 μl of water are added.

For the photoreaction, a 20-fold molar excess of DigPA is added to 15 μg of the hybridised hairpin oligonucleotide. Subsequently, the solution is illuminated under a UV lamp at 366 nm or 312 nm in an Eppendorf tube in an ice bath. The photoreaction is followed with HPLC. Within 15 minutes the photoreaction was complete.

EXAMPLE 6

Photolabelling with DigPA

For the photolabelling with DigPA, 50 μl of 1M sodium tetraborate buffer pH 8.3 and 50 μl of DigPA (2 μg/μl) were added to 2 to 5 μg of DNA in 20 μl of TE buffer and the solution was made up to 500 μl with double distilled $H_2O$. The mixture was then irradiated with a UV transilluminator for 10 minutes at 312 nm with the samples being stored on ice during this process.

The photolabelled DNA was subsequently precipitated at room temperature with 1/10 volume of 3M sodium acetate pH 5.8 and 1 volume of isopropanol and left to stand for 5 minutes. Subsequently, the DNA was centrifuged down at 10,000 rpm in an Eppendorf centrifuge, the supernatant was decanted off and the DNA precipitate was washed with 70% ethanol. After the samples had been dried, the photolabelled DNA was taken up in TE. The photolabelling of the DNA with digoxigenin was subsequently examined by agarose gel electrophoresis and dot blot assays with digoxigenin antibody conjugates.

In the gel electrophoresis, the photolabelled DNA migrates more slowly than the unlabelled DNA, which is evident in a slight shift towards the origin in the case of the photolabelled DNA band. In this method, denatured DNA is not observed in the wells of the gel.

The labelling with digoxigenin was also examined immunologically using a kit from Boehringer, Mannheim. For this purpose, the photolabelled DNA was applied to nitrocellulose membranes in various dilutions and fixed in vacuo at 80° C. Subsequently, the membrane was washed for 1 minute in buffer 1 (100 mM Tris/HCl, 150 mM NaCl pH 7.5). Then the filter was incubated for 30 minutes with 100 ml of buffer 2 (0.5% blocking reagent in buffer 1). Next it was washed in buffer 1 once again. Antibody conjugate (anti-digoxigenin antibody coupled to alkaline phosphatase) was diluted 1:5,000 to 150 mU/ml in buffer 1 and the filter was incubated for 30 minutes with 20 ml of the diluted antibody solution. Non-bound antibody was then removed by 2×15-minute washes with 100 ml of buffer 1. Subsequently, the membrane was equilibrated at room temperature for 2 minutes with 20 ml of buffer 3 (100 mM Tris/HCl, 100 mM NaCl, 50 mM $MgCl_2$ pH 9.5). The filter was incubated in the dark in a plastic bag with 10 ml of dye solution (45 μl of nitro blue tetrazolium solution and 35 μl of bromochloroindolyl phosphate in 10 ml of buffer 3). After development of the colour spots, the membrane was washed for 5 minutes with 50 ml of buffer 4 (10 mM Tris/HCl, 1 mM EDTA pH 8) in order to stop the colour reaction.

EXAMPLE 7

Photolabelling with photodigoxigenin

In photodigoxigenin, the azidophenyl group, which is coupled to digoxigenin by means of a hydrophilic spacer, reacts non-specifically with a multiplicity of compounds such as, for example, proteins and nucleic acids on mercury vapour illumination (350 to 700 nm).

Nucleic acids were labelled with photodigoxigenin according to the Boehringer method. 10 μg of photodigoxigenin solution (10 mg/ml in dimethylformamide) were added to 10 μg of DKA and the solution was made up to 40 μl with double distilled H₂O. The open tube was placed in ice-water at a distance of 10 cm underneath a Philips HPLR 400 W lamp and irradiated for 15 minutes. 60 μl of Tris/HCl, 100 mmol/l, pH 9, EDTA, 1 mmol/l, were added and then 15 μl of NaCl, 5 mol/l. The solution was then extracted twice with 100 μl of 2-butanol and the DNA was precipitated with 10 μl of LiCl, 4 mol/l, and 100 μl of pre-chilled ethanol. After 40 minutes at −70° C., the mixture was centrifuged at 12,000 g and the pellet washed with cold 70% ethanol, dried in vacuo and then dissolved in 40 μl of Tris/HCl, 10 mmol/l, EDTA, 1 mmol/l pH 8.

The photolabelling was checked both by gel electrophoresis and immunologically using a digoxigenin antibody conjugate.

In the agarose gel electrophoresis, it was observed that a large part of the photodigoxigeninised DNA WAS present in denatured form in the gel wells. By contrast, in the DigPA method described in Example 6, only one band of the photolabelled DNA is visible and no denatured DNA can be observed in the gel wells.

Immunological examination of the photodigoxigeninisation was carried out as described in Example 6.

In dot blot tests with fixed photodigoxigeninised DNA it was additionally observed that the labelling efficiency was clearly inferior to that of the very mild DigPA process described in Example 6.

We claim:

1. A labeling reagent of the formula:

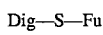

wherein

Dig represents a digoxigenin derivative of the formula:

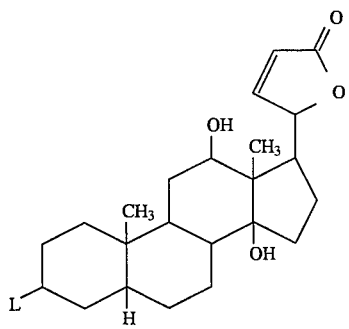

in which

L represents COO—, S—, NH— or O—;

S represents a spacer selected from the group consisting of spacers of the formulae:

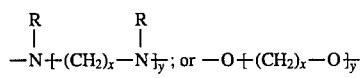

in which

R represents H, alkyl or alkoxy each having 1 to 7 carbon atoms, or aryl;

x represents a number between 2 and 7; and y represents a number between 3 and 10;

or a combination of such spacers; and

Fu represents a furocoumarin derivative selected from the group consisting of angelicin derivatives of the formula:

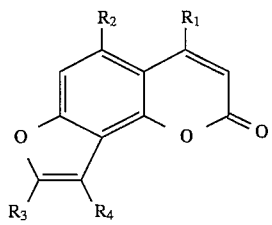

in which $R_1$, $R_2$ and $R_3$ independently represent H or alkyl having 1 to 7 carbon atoms; and $R_4$ represents H, alkyl having 1 to 7 carbon atoms and optionally substituted with hydroxyl, alkoxy having 1 to 7 carbon atoms, amino, halogen, or N-phthalimido;

and psoralen derivatives of the formula:

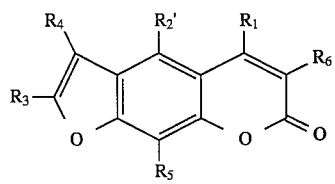

in which $R_1$, $R_3$ and $R_4$ are as indicated above; and $R_6$ represents H or alkyl having 1 to 7 carbon atoms; and $R_2$, and $R_5$ independently represent H, hydroxyl, carboxyl, carbo-$C_1$-$C_7$-alkoxy or alkoxy having 1 to 7 carbon atoms.

2. Labelling reagent according to claim 1, in which Fu is an angelicin derivative of the following general formula:

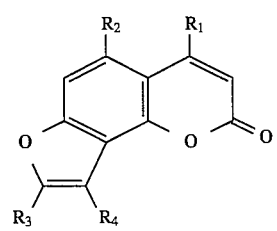

where $R_1$, $R_2$ and $R_3$, independently of each other, represent H or $C_1$-$C_7$-alkyl, and $R_4$ represents H, $C_1$-$C_7$-alkyl or a low alkyl with hydroxyl, $C_1$-$C_7$-alkoxy, amino, halo or N-phthalimido substituents.

3. Labelling reagent according to claim 1, in which Fu is a psoralen of the following general formula:

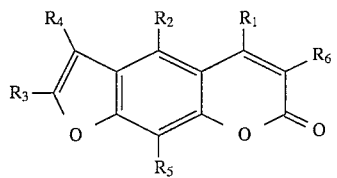

where $R_1$, $R_3$ and $R_6$, independently of each other, represent H or $C_1$–$C_7$-alkyl, $R_4$ represents H, $C_1$–$C_7$-alkyl or $C_1$–$C_7$-alkyl with hydroxyl, $C_1$–$C_7$-alkoxy, amino, halo or N-phthalimido substituents, $R_2$ and $R_5$, independently of each other, represent H, hydroxyl, carboxyl, carbo-$C_1$–$C_7$-alkoxy or $C_1$–$C_7$-alkoxy.

* * * * *